United States Patent [19]
Chiu et al.

[11] Patent Number: 5,690,662
[45] Date of Patent: Nov. 25, 1997

[54] DEVICE AND METHOD TO CREATE A SMOOTH OPENING ON A TUBULAR STRUCTURE SUCH AS AN ARTERY OR A VEIN

[75] Inventors: David Tak Wai Chiu, Bronxville, N.Y.; Heinz Rosskothen, Tea Neck, N.J.

[73] Assignee: The Trustees of Columbia University in the City of New York, New York, N.Y.

[21] Appl. No.: 541,220

[22] Filed: Oct. 12, 1995

[51] Int. Cl.⁶ .................................................. A61B 17/32
[52] U.S. Cl. ........................................... 606/184; 30/310
[58] Field of Search ................................. 606/184, 170, 606/171; 128/753, 754; 227/180.1; 30/300, 310

[56] References Cited

U.S. PATENT DOCUMENTS

| | | | |
|---|---|---|---|
| 737,293 | 8/1903 | Summerfeldt. | |
| 2,524,713 | 10/1950 | Plechas | 128/214 |
| 3,701,352 | 10/1972 | Bosworth | 606/184 |
| 3,762,416 | 10/1973 | Moss et al. | 128/305 |
| 3,958,557 | 5/1976 | Sharp et al. | 128/1 |
| 4,018,228 | 4/1977 | Goosen | 606/184 |
| 4,723,546 | 2/1988 | Zagorski | 128/305 |
| 4,867,155 | 9/1989 | Isaacson | 128/305 |
| 4,887,613 | 12/1989 | Farr et al. | 606/159 |
| 4,895,166 | 1/1990 | Farr et al. | 128/751 |
| 5,007,917 | 4/1991 | Evans | 606/170 |
| 5,071,412 | 12/1991 | Noda | 604/268 |
| 5,084,052 | 1/1992 | Jacobs | 606/79 |
| 5,112,299 | 5/1992 | Pascaloff | 604/22 |
| 5,129,913 | 7/1992 | Ruppert | 606/184 |
| 5,160,318 | 11/1992 | Shuler | 604/22 |
| 5,222,965 | 6/1993 | Haughton | 606/159 |

Primary Examiner—Michael H. Thaler
Attorney, Agent, or Firm—John P. White

[57] ABSTRACT

An apparatus for creating a substantially circular hole in a wall of a vessel of a patient is provided, comprising an elongated circular knife with a proximal end, a distal end with a circular knife edge, and an inner channel, an elongated probe with a proximal end and a distal end, the elongated probe being disposed within the inner channel of the elongated circular knife and being adapted to be moveable axially and rotatably with respect to the elongated circular knife, and a bar formed on the distal end of the elongated probe, the bar being substantially perpendicular to the elongated probe, whereby when the bar is inserted in the vessel through a slit in the wall of the vessel, the elongated probe and the bar may be rotated with respect to the circular knife edge of the elongated cylindrical knife to form a substantially circular hole in the wall of the vessel. A method for creating a substantially circular hole in a wall of a vessel of a patient is also provided.

17 Claims, 4 Drawing Sheets

5,690,662

DEVICE AND METHOD TO CREATE A SMOOTH OPENING ON A TUBULAR STRUCTURE SUCH AS AN ARTERY OR A VEIN

BACKGROUND OF THE INVENTION

The present invention relates to an apparatus and method for creating a circular hole in the wall of a vessel for end-to-side connection.

The end-to-side connection, or anastomosis, of arteries, veins, and the like is well known in the art. Such vessels may be connected by any well known method such as suturing or gluing, for example.

The instant invention provides an apparatus and method to create a smooth, regular, repeatable, and predictable hole in the wall of a vessel in order to allow a doctor to easily perform such anastomosis.

SUMMARY OF THE INVENTION

It is an object of the present invention to provide an apparatus for creating a smooth, regular, repeatable, and predictable hole in the wall of a vessel.

It is a further object of the present invention to provide a method for creating a smooth, regular, repeatable, and predictable hole in the wall of a vessel.

According to one aspect of the present invention an apparatus for creating a substantially circular hole in a wall of a vessel of a patient is provided, comprising an elongated circular knife with a proximal end, a distal end with a circular knife edge, and an inner channel, an elongated probe with a proximal end and a distal end, said elongated probe being disposed within said inner channel of said elongated circular knife and being adapted to be moveable axially and rotatably with respect to said elongated circular knife, and a bar formed on the distal end of the elongated probe, said bar being substantially perpendicular to said elongated probe, whereby when said bar is inserted in the vessel through a slit in the wall of the vessel, the elongated probe and the bar may be rotated with respect to the circular knife edge of said elongated cylindrical knife to form a substantially circular hole in the wall of the vessel.

According to another aspect of the present invention a method for creating a substantially circular hole in a wall of a vessel of a patient is provided, comprising cutting a slit in the wall of the vessel, inserting a T-bar formed on the distal end of an elongated probe through the slit in the wall of the vessel, and rotating the elongated probe and the bar with respect to a circular knife disposed around said elongated probe and adjacent said bar to form a substantially circular hole in the wall of the vessel.

According to another aspect of the instant invention a veterinary apparatus for creating a substantially circular hole in a wall of a vessel of an animal is provided, comprising an elongated circular knife with a proximal end, a distal end with a circular knife edge, and an inner channel, an elongated probe with a proximal end and a distal end said elongated probe being disposed within said inner channel of said elongated circular knife and being adapted to be moveable axially and rotatably with respect to said elongated circular knife, and a bar formed on the distal end of the elongated probe, said T-bar being substantially perpendicular to said elongated probe, whereby when said bar is inserted in the vessel through a slit in the wall of the vessel, the elongated probe and the bar may be rotated with respect to the circular knife edge of said elongated cylindrical knife to form a substantially circular hole in the wall of the vessel.

According to another aspect of the present invention a veterinary method for creating a substantially circular hole in a wall of a vessel of an animal is provided, comprising cutting a slit in the wall of the vessel, inserting a bar formed on a distal end of an elongated probe through the slit in the wall of the vessel, and rotating the elongated probe and the bar with respect to a circular knife disposed around said elongated probe and adjacent said bar to form a substantially circular hole in the wall of the vessel. The vessel may be an artery or a vein.

These and other advantages will become apparent from the detailed description accompanying the claims and attached drawing figures.

DETAILED DESCRIPTION OF THE PREFERRED EMBODIMENTS

Figure 1:
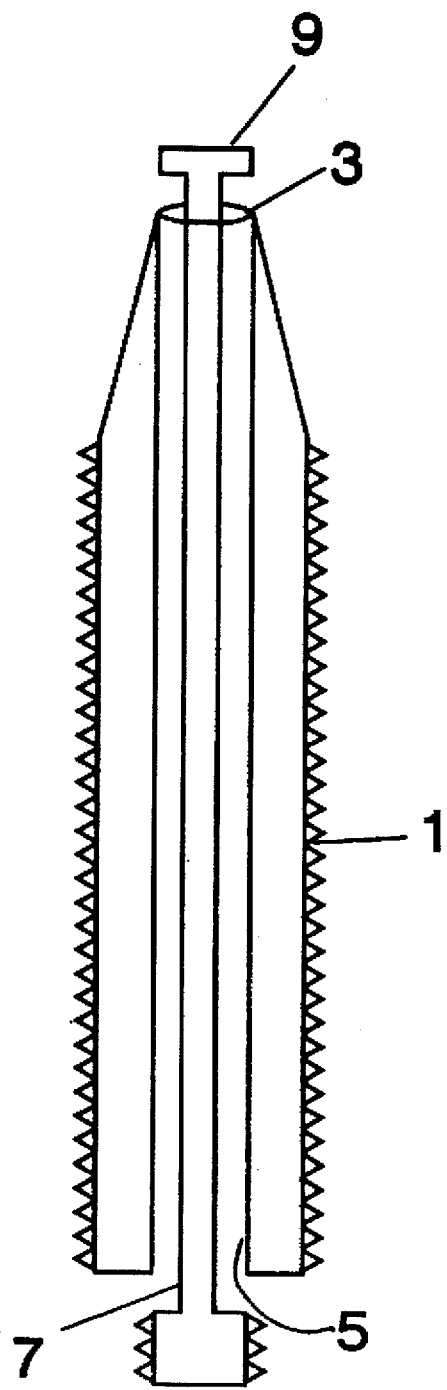
FIG. 1 shows a cross-sectional view of an apparatus to create a circular hole in the wall of a vessel for end-to-side connection according to an embodiment of the present invention.

According to one aspect of the present invention an apparatus for creating a substantially circular hole in a wall of a vessel of a patient is provided, comprising an elongated circular knife with a proximal end, a distal end with a circular knife edge, and an inner channel, an elongated probe with a proximal end and a distal end, said elongated probe being disposed within said inner channel of said elongated circular knife and being adapted to be moveable axially and rotatably with respect to said elongated circular knife, and a bar formed on the distal end of the elongated probe, said bar being substantially perpendicular to said elongated probe, whereby when said bar is inserted in the vessel through a slit in the wall of the vessel, the elongated probe and the bar may be rotated with respect to the circular knife edge of said elongated cylindrical knife to form a substantially circular hole in the wall of the vessel.

The apparatus may further comprise means for gripping an exterior surface of the elongated circular knife and means for gripping the proximal end of the elongated probe. The means for gripping the exterior surface of the elongated circular knife may comprise a high-friction surface. The high-friction surface may comprise a knurled surface. The means for gripping the proximal end of the elongated probe may comprise a knob. The knob may include a high-friction gripping surface and the high-friction gripping surface may comprise a knurled surface. The elongated circular knife, said elongated probe, and said bar may be formed of stainless steel. The vessel may be an artery or a vein.

According to another aspect of the present invention a method for creating a substantially circular hole in a wall of a vessel of a patient is provided, comprising cutting a slit in the wall of the vessel, inserting a bar formed on the distal end of an elongated probe through the slit in the wall of the vessel, and rotating the elongated probe and the bar with respect to a circular knife disposed around said elongated probe and adjacent said T-bar to form a substantially circular hole in the wall of the vessel. The vessel may be an artery or a vein.

According to another aspect of the instant invention a veterinary apparatus for creating a substantially circular hole in a wall of a vessel of an animal is provided, comprising an elongated circular knife with a proximal end, a distal end with a circular knife edge, and an inner channel, an elongated probe with a proximal end and a distal end, said elongated probe being disposed within said inner channel of said elongated circular knife and being adapted to be moveable axially and rotatably with respect to said elongated circular knife, and a T-bar formed on the distal end of the elongated probe, said T-bar being substantially perpendicular to said elongated probe, whereby when said T-bar is inserted in the vessel through a slit in the wall of the vessel, the elongated probe and the T-bar may be rotated with respect to the circular knife edge of said elongated cylindrical knife to form a substantially circular hole in the wall of the vessel.

According to another aspect of the present invention a veterinary method for creating a substantially circular hole in a wall of a vessel of an animal is provided, comprising cutting a slit in the wall of the vessel, inserting a T-bar formed on a distal end of an elongated probe through the slit in the wall of the vessel, and rotating the elongated probe and the T-bar with respect to a circular knife disposed around said elongated probe and adjacent said T-bar to form a substantially circular hole in the wall of the vessel. The vessel may be an artery or a vein.

Referring now to FIG. 1, an apparatus according to an embodiment of the invention is shown in which elongated circular knife 1 has a circular knife edge 3 and an inner channel 5. An elongated probe 7 is disposed within the inner channel 5 of the elongated circular knife 1. This elongated probe 7 is adapted to be moveable both axially and rotatably with respect to the elongated circular knife 1.

Further, the elongated probe 7 has a linear-bar 9 formed on the end adjacent the circular knife edge 3. This bar 9 is mounted substantially perpendicular to the elongated probe 7 such that said elongated probe 7 and said bar 9 form a T.

Referring now to FIGS. 2(a)-2(d), wherein the same reference numerals apply to the same elements of FIG. 1, when the bar 9 is inserted in a tubular structure 20, such as an artery or a vein, through a slit 22 in the tubular structure wall 21, the elongated probe 7 and the bar 9 may be rotated with respect to the circular knife edge 3 of the elongated cylindrical knife 1 to form a substantially circular hole in the tubular structure wall 20.

Figure 2A:
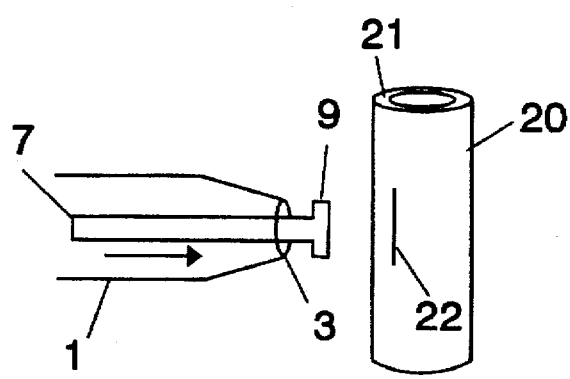
FIGS. 2(a)–2(d) show the use of the embodiment of FIG. 1.
Figure 2B:
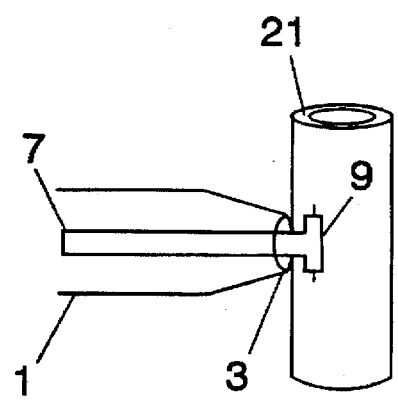
Figure 2C:
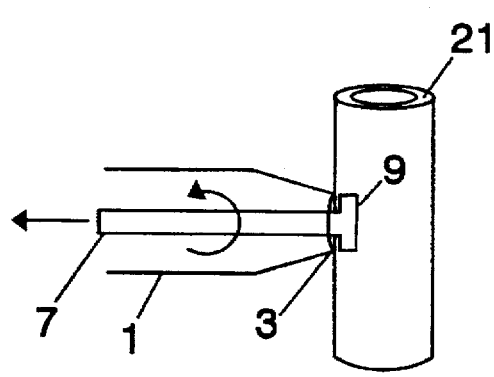
Figure 2D:
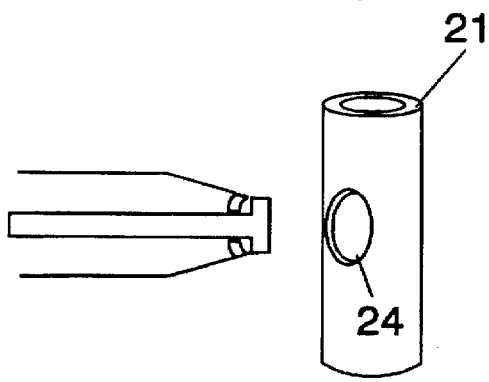

More particularly, FIG. 2(a) shows the elongated probe 7 and the bar 9 extended axially away from the elongated circular knife 1. FIG. 2(b) shows the bar, still axially extended away from the circular knife 1, inserted into the slit 22. FIG. 2(c) shows the elongated probe 7 and the bar 9 pulled back towards the circular knife edge 3 whereby the tubular structure wall is sandwiched between the circular knife edge 3 and the bar 9. Further, in this FIG. 2(c) the elongated probe 7 and the bar 9 are shown being rotated with respect to the circular knife edge 3. Finally, FIG. 2(d) shows the circular knife 1, the elongated probe 7 and the bar 9 being moved away from the tubular structure wall 20 to leave a substantially circular hole 24.

Figure 3:
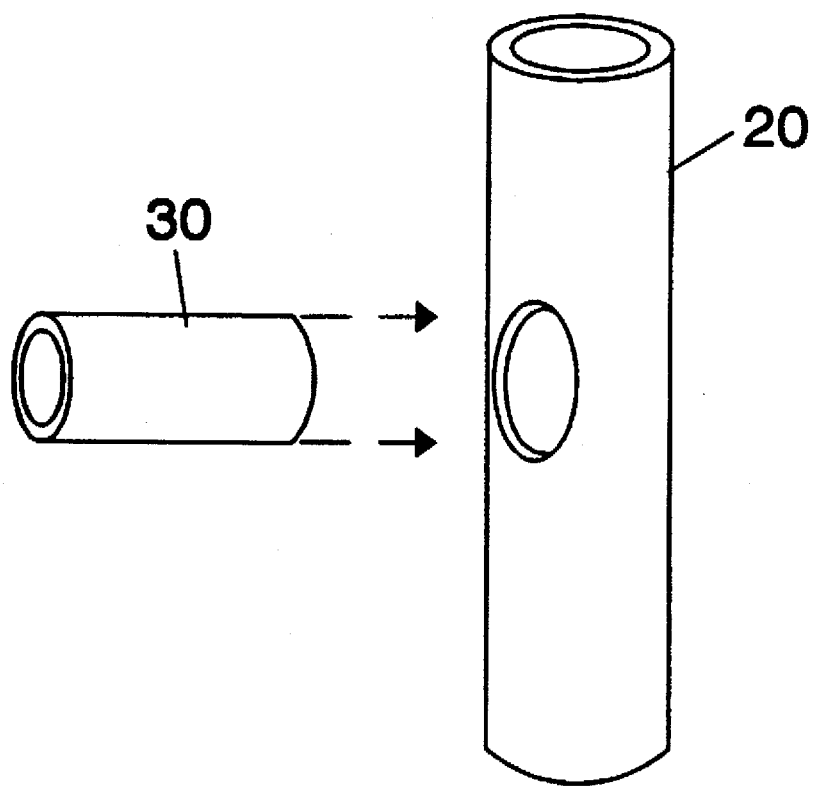
FIG. 3 shows an end-to-side connection which may result from the use of the instant invention.

Referring now to FIG. 3, wherein the same reference numerals apply to the same elements of FIGS. 2(a)-2(d), a second tubular structure 30 may be attached to the tubular structure 20 in an end-to-side manner.

Figure 4:
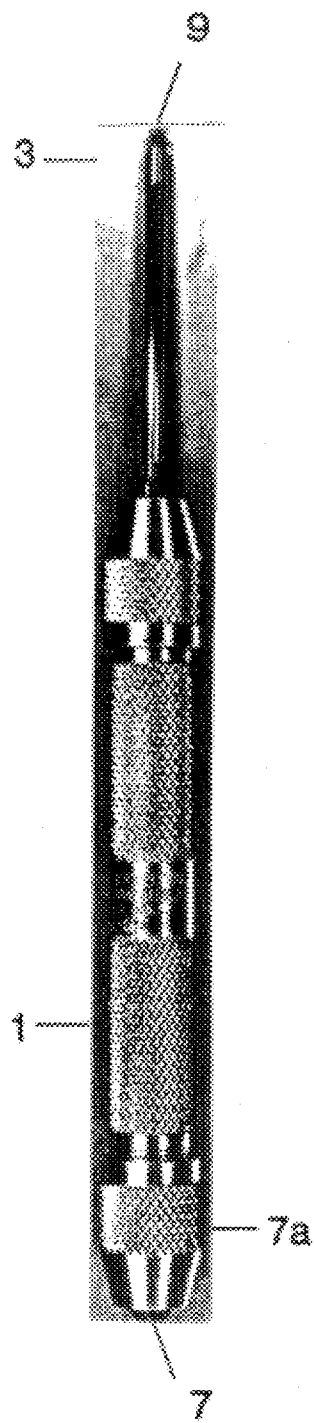
FIG. 4 shows another view of the apparatus according to the invention.

Referring now to FIG. 4, wherein the same reference numerals apply to the same elements of FIG. 1, the exterior of the circular knife 1 may be knurled. In addition, the proximal end of the elongated probe 7, which is gripped by the user, may have a knob 7a and may also be knurled.

Although the present invention is described by reference to particular embodiments thereof, many changes and modifications of the invention may become apparent to those skilled in the art without departing from the spirit and scope of the invention, which is only limited by the appended claims. Therefore, the embodiments shown and described are only illustrative, not restrictive.

What is claimed is:

1. An apparatus for creating a substantially circular hole in a wall of a vessel of a patient, comprising:
   an elongated circular knife with a proximal end, a distal end with a circular knife edge, and an inner channel;
   an elongated probe with a proximal end and a distal end, said elongated probe being disposed within said inner channel of said elongated circular knife and being adapted to be moveable axially and rotatably with respect to said elongated circular knife; and
   a linear bar member formed on the distal end of the elongated probe, said linear bar member being substantially perpendicular to said elongated probe, whereby when said linear bar member is inserted in the vessel through a slit in the wall of the vessel, the elongated probe and the linear bar member may be rotated with respect to the circular knife edge of said elongated cylindrical knife to form a substantially circular hole in the wall of the vessel.

2. The apparatus of claim 1, further comprising means for gripping an exterior surface of the elongated circular knife and means for gripping the proximal end of the elongated probe.

3. The apparatus of claim 2, wherein said means for gripping the exterior surface of the elongated circular knife comprises a high-friction surface.

4. The apparatus of claim 3, wherein said high-friction surface comprises a knurled surface.

5. The apparatus of claim 2, wherein said means for gripping the proximal end of the elongated probe comprises a knob.

6. The apparatus of claim 5, wherein said knob includes a high-friction gripping surface.

7. The apparatus of claim 6, wherein said high-friction gripping surface comprises a knurled surface.

8. The apparatus of claim 1, wherein said elongated circular knife, said elongated probe, and said linear bar member are formed of stainless steel.

9. The apparatus of claim 1, wherein said vessel is an artery.

10. The apparatus of claim 1, wherein said vessel is a vein.

11. A method for creating a substantially circular hole in a wall of a vessel of a patient, comprising:
    cutting a slit in the wall of the vessel;
    inserting a linear bar member formed on a distal end of an elongated probe through the slit in the wall of the vessel said linear bar member being substantially perpendicular to said elongated probe; and
    rotating the elongated probe and the linear bar member with respect to a circular knife disposed around said elongated probe and adjacent said linear bar member to form a substantially circular hole in the wall of the vessel.

12. The method of claim 11, wherein said vessel is an artery.

13. The method of claim 11, wherein said vessel is a vein.

14. A veterinary apparatus for creating a substantially circular hole in a wall of a vessel of an animal, comprising:

an elongated circular knife with a proximal end, a distal end with a circular knife edge, and an inner channel;

an elongated probe with a proximal end and a distal end, said elongated probe being disposed within said inner channel of said elongated circular knife and being adapted to be moveable axially and rotatably with respect to said elongated circular knife; and a linear bar member formed on the distal end of the elongated probe, said linear bar member being substantially perpendicular to said elongated probe, whereby when said linear bar member is inserted in the vessel through a slit in the wall of the vessel, the elongated probe and the linear bar member may be rotated with respect to the circular knife edge of said elongated cylindrical knife to form a substantially circular hole in the wall of the vessel.

15. A veterinary method for creating a substantially circular hole in a wall of a vessel of an animal, comprising:

cutting a slit in the wall of the vessel;

inserting a linear bar member formed on a distal end of an elongated probe through the slit in the wall of the vessel said linear bar member being substantially perpendicular to said elongated probe; and rotating the elongated probe and the linear bar member with respect to a circular knife disposed around said elongated probe and adjacent said linear bar member to form a substantially circular hole in the wall of the vessel.

16. The method of claim 15, wherein said vessel is an artery.

17. The method of claim 15, wherein said vessel is a vein.

* * * * *

UNITED STATES PATENT AND TRADEMARK OFFICE
CERTIFICATE OF CORRECTION

PATENT NO. : 5,690,662
DATED : November 25, 1997
INVENTOR(S) : David Tak Wai Chiu and Heinz Rosskothen It is certified that error appears in the above-identified patent and that said Letters Patent is hereby corrected as shown below:

column 1, line 48: "a T-bar formed" should read --a bar formed--
           line 59: "distal end said" should read --distal end, said--
           line 64: "said T-bar" should read --said bar--
column 3, line 1: "said T-bar" should read --said bar--
           line 13: "a T-bar formed" should read --a bar formed--
           line 14: "said T-bar being" should read --said bar being--
           line 15: "said T-bar is" should read --said bar is--
           line 17: "the T-bar may" should read --the bar may--
           line 24: "a T-bar" should read --a bar--
           line 27: "the T-bar" should read --the bar--
           line 28: "said T-bar" should read --said bar--
column 4, line 58: "the vessel" should read --the vessel,--
column 6, line 6: "the vessel" should read --the vessel,--

Signed and Sealed this

Twentieth Day of April, 1999

*Attest:*

Q. TODD DICKINSON

*Attesting Officer*        *Acting Commissioner of Patents and Trademarks*